Figure 1:
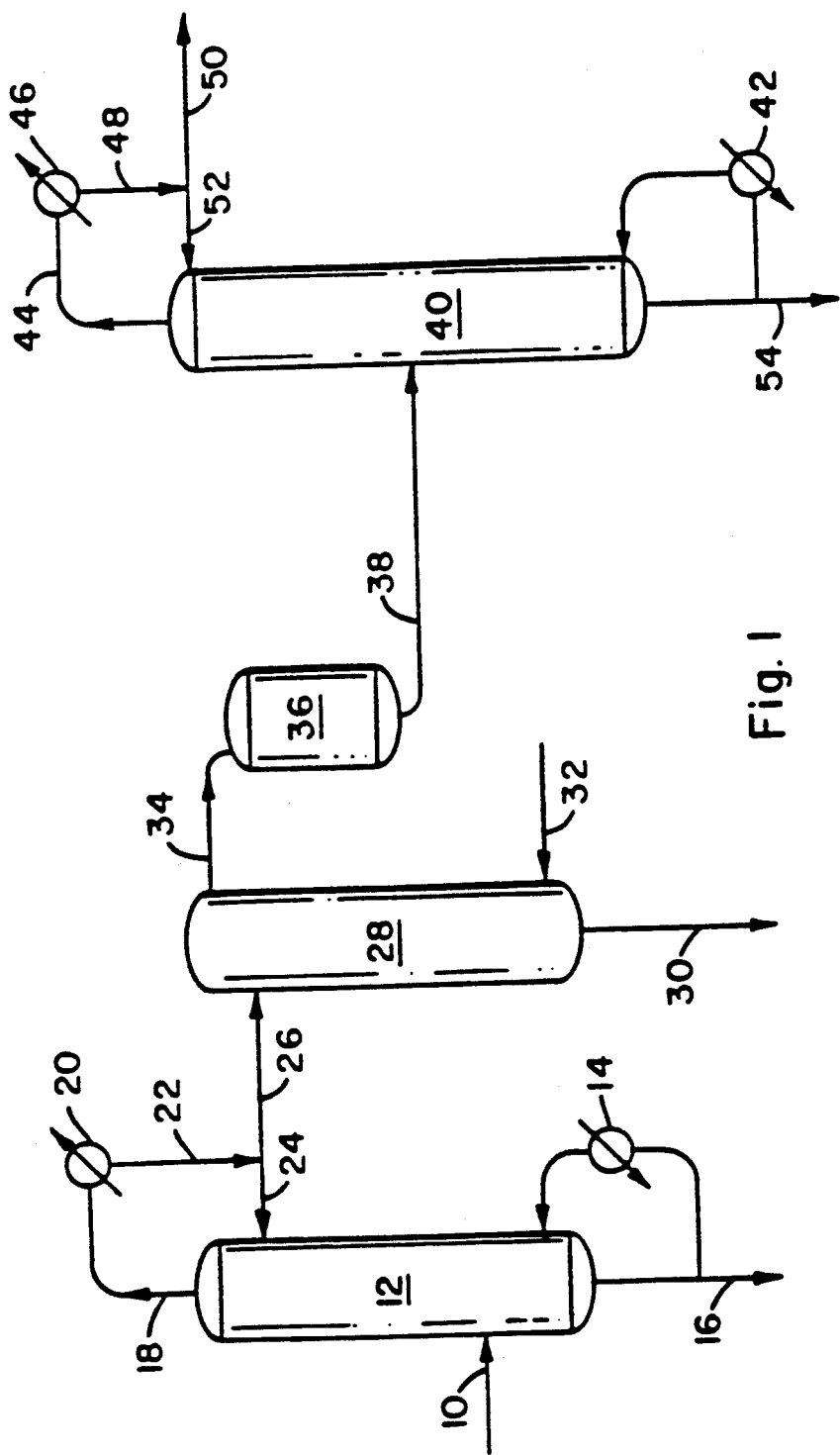

United States Patent [19]

Zoeller et al.

[11] Patent Number: 5,057,192
[45] Date of Patent: Oct. 15, 1991

[54] ACETONE REMOVAL FROM ACETIC ANHYDRIDE PRODUCTION PROCESS

[75] Inventors: Joseph R. Zoeller; Steven L. Cook; Charles E. Outlaw; Robert M. Schisla, Jr., all of Kingsport, Tenn.

[73] Assignee: Eastman Kodak Company, Rochester, N.Y.

[21] Appl. No.: 662,158

[22] Filed: Feb. 28, 1991

Related U.S. Application Data

[63] Continuation-in-part of Ser. No. 616,528, Nov. 2, 1990, abandoned, which is a continuation-in-part of Ser. No. 590,838, Oct. 1, 1990, abandoned.

[51] Int. Cl.[5] ............... B01D 3/40; C07C 45/83; C07C 51/12; C07C 53/12
[52] U.S. Cl. ...................... 203/46; 203/81; 203/83; 203/96; 203/97; 203/DIG. 19; 560/248; 567/608; 567/891; 568/411; 570/263
[58] Field of Search .............. 203/46, 93, 97, 96, 203/83, 81, 76, DIG. 19, 99; 562/891, 898, 608; 568/411, 387; 560/248; 570/263

[56] References Cited

U.S. PATENT DOCUMENTS

| | | | |
|---|---|---|---|
| 3,409,513 | 11/1968 | Hamlin et al. | 203/46 |
| 3,531,376 | 9/1970 | Minoda et al. | 203/46 |
| 4,046,807 | 9/1977 | Kuckertz | 562/891 |
| 4,252,748 | 2/1981 | Hoch et al. | 203/60 |
| 4,374,070 | 2/1983 | Larkins et al. | 562/891 |
| 4,444,624 | 4/1984 | Erpenbach et al. | 203/61 |
| 4,559,183 | 12/1985 | Hewlett | 562/891 |
| 4,717,454 | 1/1988 | Erpenbach et al. | 203/49 |

FOREIGN PATENT DOCUMENTS

74506 3/1983 European Pat. Off. ............ 568/411

*Primary Examiner*—Wilbur Bascomb, Jr.
*Attorney, Agent, or Firm*—J. Frederick Thomsen; William P. Heath, Jr.

[57] ABSTRACT

Disclosed is an improved process for the removal of acetone from a production system wherein acetic anhydride is produced by contacting a mixture containing methyl iodide and methyl acetate and/or dimethyl ether with carbon monoxide in the presence of a carbonylation catalyst or catalyst system. The process involves a water-methyl iodide extraction step wherein acetone is separated from a mixture of methyl acetate, methyl iodide and acetone.

7 Claims, 2 Drawing Sheets

Fig. 1

ACETONE REMOVAL FROM ACETIC ANHYDRIDE PRODUCTION PROCESS

This application is a continuation-in-part of copending application Ser. No. 07/616,528, filed Nov. 2, 1990, now abandoned; which is a continuation-in-part of copending application Ser. No. 07/590,838 filed Oct. 1, 1990 now abandoned.

This invention pertains to a process of removing acetone formed during the production of acetic anhydride or a mixture of acetic anhydride and acetic acid by carbonylation processes.

The preparation of acetic anhydride by contacting a mixture comprising methyl iodide and methyl acetate and/or dimethyl ether with carbon monoxide in the presence of a rhodium catalyst has been reported extensively in the patent literature. See, for example, U.S. Pat. Nos. 3,927,078, 4,046,807, 4,374,070 and 4,559,183 and European Patents 8396 and 87,870. These patents disclose that the reaction rate can be increased if the catalyst system includes a promoter such as certain amines, quaternary ammonium compounds, phosphines and inorganic compounds such as lithium compounds. The crude or partially-refined product obtained from such acetic anhydride processes typically comprises a mixture of acetic anhydride and acetic acid as a result of the use of acetic acid as a process solvent and/or the co-production of acetic acid by including methanol and/or water in the feed to the carbonylation reactor.

Acetone is formed in the above-described carbonylation process but since it accumulates in the acetic anhydride production system to a maximum level of about 5 weight percent, based on the total weight of the contents of the carbonylation reactor, its removal is not essential to the operation of the manufacturing system. Furthermore, the value of the relatively small amount of acetone formed is not sufficient to justify the cost of its separation and purification to a sales grade acetone product. Although the mechanism by which acetone achieves a maximum steady state concentration is not known, it generally has been assumed that it is consumed in the formation of process "tars".

A number of acetone removal processes have been described in the patent literature although there has been no apparent economic incentive for using them. U.S. Pat. No. 4,252,748 describes a complex procedure in which all of the methyl iodide, all of the acetone, and some methyl acetate is removed from a low-boiling, recycle stream. The stream is then fractionated to obtain a methyl acetate acetone rich stream which is then subjected to an azeotropic distillation with pentane, yielding methyl acetate and an acetone-containing pentane stream. The acetone is extracted with water and the pentane is recycled. This complex scheme requires the processing of large volumes of effluent and entails a total of 5 operational steps (4 distillations and an extraction). Furthermore, one would expect that a portion of the methyl iodide, the most valuable process material in this stream, would accumulate in the pentane.

U.S. Pat. No. 4,444,624 describes a system similar to the process of the '748 patent wherein a portion of the low boiler effluent is distilled with a countercurrent of acetic acid to give a fraction rich in methyl iodide and methyl acetate and a second fraction rich in methyl acetate and acetone, both of which contain very large quantities of acetic acid. The acetone-containing fraction is further distilled to give a fraction containing primarily methyl acetate and most of the acetone. The ratio of methyl acetate to acetone is very high, generally about 50:1. The acetone is removed from the larger amount of methyl acetate by azeotropic distillation with pentane and subsequent aqueous extraction to remove the acetone. This process employs very large volumes of acetic acid, generally around 1 part of acetic acid for every 2 parts of low boiler fraction to be extractively distilled, and entails 4 operational steps (3 distillations and extraction.) This process requires one less step than the process of the '748 patent only because it does not attempt to purify the acetone from the acetone-water mixture. The processes of both the '748 and '624 patents require the use of pentane which introduces the risk of product contamination since pentane is not otherwise used in the acetic anhydride production system.

Finally, according to U.S. Pat. No. 4,717,454, acetone may be removed by converting it to condensation products which may be removed from the production system in the distillation as part of the ethylidene diacetate.

The process of the present invention provides for the removal of acetone from a production system in which acetic anhydride is produced by contacting carbon monoxide with a mixture comprising methyl iodide and methyl acetate and/or dimethyl ether in the presence of a catalyst system and acetic acid by means of the steps comprising:

(1) obtaining from the production system a low-boiling stream comprising methyl acetate, methyl iodide, acetic acid and acetone;

(2) distilling the stream of Step (1) to obtain:
  (a) an overhead stream comprising methyl acetate, methyl iodide and acetone; and
  (b) an underflow stream comprising methyl acetate, methyl iodide, acetone and essentially all of the acetic acid;

(3) extracting the Step(2)(a) stream with water to obtain:
  (a) a methyl iodide phase containing methyl acetate; and
  (b) an aqueous phase containing methyl acetate, methyl iodide and acetone; and (4) distilling the aqueous phase to obtain:
  (a) a vapor phase comprising methyl acetate, methyl iodide and minor amounts of acetone and water; and
  (b) an aqueous stream containing methyl acetate and acetone.

Operation of the described acetone removal process results in a decrease in the amount of acetone present in the carbonylation reactor, e.g., acetone concentrations of about 2.0 to 2.5 weight percent based on the total weight of the reactor contents. Operation of the carbonylation process in the presence of lower levels of acetone results in the production of acetic anhydride containing lower levels of "reducing substances." One of the purity specifications for acetic anhydride which is difficult to achieve is the level of "reducing substances", a specification which is particularly important to manufacturers of cellulose acetate. A typical specification requires a permanganate reducing substances test value of at least 30 minutes according to a modification of the Substances Reducing Permanganate Test, American Chemical Society Specifications published in Reagent Chemicals, 6th Ed., American Chemical Society, Washington, D.C., pp. 66 and 68. The use of acetic anhydride containing lower levels of reducing substances decreases the amount of bleaching agents required in cellulose acetate manufacturing processes, thus lowering the manufacturing costs and further enhancing the value of the acetic anhydride. The process provided by our invention provides a means for producing, by the carbonylation processes described above, acetic anhydride which will more consistently pass the reducing substances test.

Figure 2:
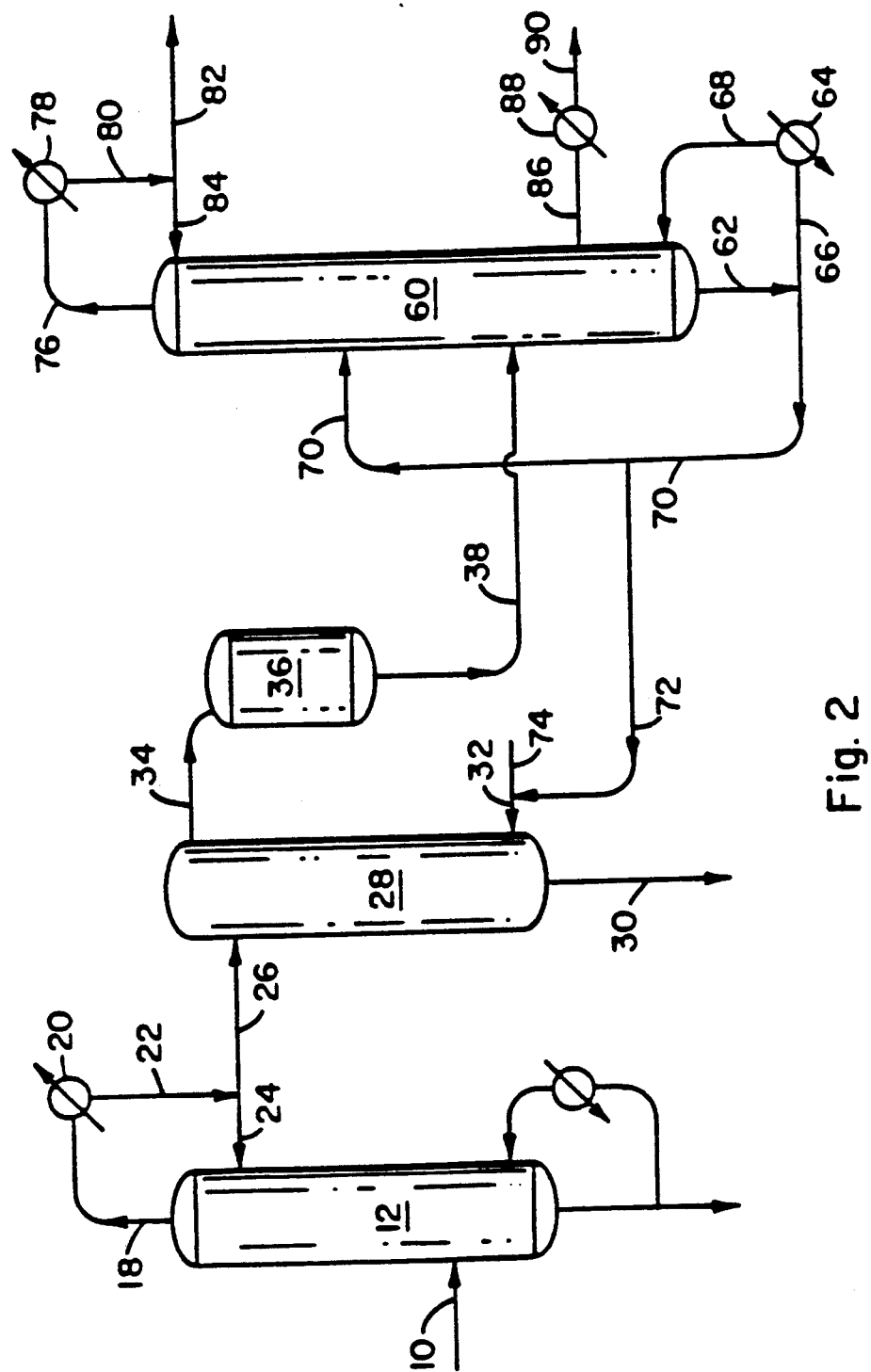

The accompanying FIGS. 1 and 2 are process flow diagrams illustrating two systems embodying the principles of the process of the present invention. It is, of course, possible that the acetone removal process may be operated by modifying the specific processes illustrated by the Figures. The boiling points (°C.) of the volatile materials employed in the process are:

| Material | B.P. |
|---|---|
| MeI | 42.5 |
| Acetone | 56.2 |
| MeOAc | 57.0 |
| MeI/Acetone | 42.4 |
| MeI/MeOAc | 42.1 |
| MeOAc/Acetone | 55.8 | wherein MeI is methyl iodide, MeOAc is methyl acetate, and MeI/Acetone, MeI/MeOAc and MeOAC/Acetone are constant boiling mixtures (binary azeotropes) consisting of, by weight, 95% methyl iodide and 5% acetone, 97.3% methyl iodide and 2.7 methyl acetate, and 50% methyl acetate and 50% acetone, respectively.

Referring to FIG. 1, a low-boiling mixture comprising methyl acetate, methyl iodide, acetic acid and acetone is fed by conduit 10 to distillation column 12. The low boiling mixture may be obtained from the acetic anhydride production system described in Example 1 of U.S. Pat. No. 4,374,070, as well as other acetic anhydride manufacturing processes. The low boiling mixture is the portion of the reactor effluent remaining after removal of the catalyst components, a substantial amount of the low boiling components and essentially all of the acetic anhydride and higher boiling by-products. Typically, the low boiling mixture consists of about 75 to 45 weight percent methyl acetate, 30 to 15 weight percent methyl iodide and 20 to 5 weight percent acetic acid with the concentration of the acetone varying from about 8 to 4 weight percent, depending on the length of time the acetone removal process has been operated. The mixture also may contain a trace, e.g., about 0.1 to 0.5 weight percent, of acetic anhydride. While the mixture may contain significant amounts, e.g., 30 to 40 weight percent, of acetic anhydride, our process normally is carried out using a mixture from which substantially all of the acetic anhydride and other high boilers such as ethylidene diacetate have been removed elsewhere in the production system.

Distillation column 12 is operated at ambient pressure, a base temperature of about 60° to 70° C. maintained by a heat source such as reboiler 14, and a top temperature of about 40° to 50° C. to fractionate the low boiling mixture into (1) an overhead stream comprising methyl acetate, methyl iodide and acetone and (2) an underflow stream, i.e., a base product stream, comprising methyl acetate, essentially all of the acetic acid, e.g., at least 95 weight percent of the acetic acid fed to the column, and acetone. The underflow stream is removed from distillation column 12 via conduit 16 and may be recycled to the carbonylation reactor along with additional methyl acetate, methyl iodide and catalyst components. The primary function of column 12 is to remove all, or essentially all, of the acetic acid from the low boiling mixture. To accomplish this objective, a substantial portion of the methyl iodide and acetone fed to column 12 is underflowed with the acetic acid.

The vaporized overhead stream is removed from distillation column 12 by means of conduit 18 and passed through condenser 20 wherein substantially all of the stream is converted to a liquid. A portion of the condensate from condenser 20 may be returned via lines 22 and 24 as reflux to distillation column 12. The remainder of the condensate is fed by means of conduits 22 and 26 to the upper portion of extraction column 28. Typical reflux ratios for the condensate (volume of conduit 24:volume of conduit 26) are from about 2:1 to 4:1. Water is fed through line 32 located near the bottom of extraction column 28 which is equipped with four beds packed with 0.625 inch pall ring packing material. The upwardly-flowing water extracts essentially all, e.g., at least 98 weight percent, of the acetone and a substantial portion, e.g., about 92 to 99 weight percent, of the methyl acetate. A small amount, e.g., about 5 weight percent, of the methyl iodide fed to the extractor overflows with the aqueous phase. Most of the methyl iodide containing the remainder of the methyl acetate is removed from the base of extraction column 28 via conduit 30 and may be recycled to the carbonylation reactor or used as the methyl iodide source in the tar removal process described in U.S. Pat. No. 4,388,217. The methyl iodide stream obtained from extractor 28 typically has a purity of at least 95 weight percent and preferably at least 98 weight percent.

The aqueous phase overflows extraction column 28 at or near the top and is transported through conduit 34, water extract tank 36 and conduit 38 to the mid-section of fractional distillation column 40. Column 40 contains two packed beds consisting of 0.625 pall rings and is operated at approximately atmospheric pressure, at a base temperature of about 98° to 105° C. maintained by heat source 42 and a top temperature of about 50° to 55° C. A vapor stream comprising methyl acetate, methyl iodide, and minor amounts of acetone and water is recovered from the top section of distillation column 40 via conduit 44, condensed in condenser 46, and the resulting condensate may be recycled to the carbonylation process by means of lines 48 and 50. A portion of the condensate from condenser 44 normally is returned to distillation column 40 via lines 48 and 52.

An aqueous stream comprised of water, methyl acetate and most of the acetone, e.g., at least 75 weight percent of the acetone fed to distillation column 40, is removed as a liquid from distillation column 40 through line 54 and transported to a conventional waste water treatment plant. The acetone removal system may be operated in a manner that produces a process effluent via line 54 which contains a methyl acetate:acetone weight ratio of not more than about 6, and preferably not more than about 3. Furthermore, operation of the system provides for recovery of at least 95 weight percent, normally at least 99 weight percent, of the methyl iodide, the most valuable of the chemicals fed to the system. Thus, the amount of iodine present in the process effluent removed from the system via line 54 does not exceed 200 parts per million, normally less than 100 ppm.

Typical compositions of the conduits and lines of FIG. 1 are given below wherein the methyl acetate (MeOAc), methyl iodide (MeI), acetic acid (HOAc), acetone and water components of each stream are given as weight percentages based on the total weight of the stream.

| Conduit | Components | | | | |
|---|---|---|---|---|---|
| | MeOAc | MeI | HOAc | Acetone | Water |
| 16 | 30–90 | 10–40 | 1–25 | 1–20 | 0 |
| 26 | 3–15 | 75–98 | 0–1 | 0.5–6 | 0–1 |
| 30 | 0–15 | 85–100 | 0–1 | 0–2 | 0–2 |
| 38 | 0–8 | 0–20 | 0–1 | 0.5–4 | 70–100 |
| 50 | 0–65 | 0–98 | 0–2 | 0.5–6 | 0–5 |
| 54 | 0–5 | 0–2 | 0–1 | 0.5–3 | 89–100 |

FIG. 2 represents a modification of the process depicted in FIG. 1. With reference to FIG. 2, the aqueous phase which overflows extraction column 28 is fed via line 34, water extract tank 36 and line 38 to the lower section of extractive distillation column 60 wherein a liquid phase consisting essentially of water containing a minute amount of acetone collects at the bottom of the column. A liquid phase is drained from the base of column 60 through conduit 62 and a portion is fed to heat source 64 by conduit 66 and recycled to the base of the column via conduit 68 to maintain a base temperature of about 90° to 95° C. The remainder of the liquid phase is recycled by means of conduit 70 to the upper portion of extractive distillation column 60, i.e., at a point above the feed of the aqueous phase from extractor 36. Optionally, a portion, e.g., up to about 60 weight percent, of the liquid phase transported by conduit 70 may be recycled to extractor 28 by conduits 72 and 32 for use as the water source for the extractor along with water provided by conduit 74.

In the operation of the extractive distillation, a vapor phase containing primarily methyl acetate and methyl iodide with minor amounts of acetone and water accumulates in the upper portion of column 60 and is removed at or near the top of column 60 by conduit 76. The vapor of conduit 76 is condensed by heat exchanger 78 and returned to the carbonylation process by means of conduits 80 and 82. A portion of the condensate from heat exchanger 78 may be returned to column 60 via conduits 80 and 84 at a point near the top.

In this embodiment of our invention, an aqueous phase in the form of a second vapor phase consisting essentially of methyl acetate, acetone, typically at least 80 weight percent of the acetone fed via conduit 38, and water accumulates in the lower section of column 60. The aqueous phase is removed as a second stream of vapor from the lower portion of column 60 by conduit 86, condensed in condenser 88 and transported by conduit 90 to a suitable industrial waste treatment plant.

Typical compositions of the conduits and lines of the flow diagram as modified in FIG. 2 are given below wherein the methyl acetate (MeOAc), methyl iodide (MeI), acetic acid (HOAc), acetone and water components of each stream are given as weight percentages based on the total weight of the stream.

| Conduit | Components | | | | |
|---|---|---|---|---|---|
| | MeOAc | MeI | HOAc | Acetone | Water |
| 16 | 30–90 | 10–40 | 1–25 | 1–20 | 0 |
| 62 | 0–1 | 0–0.5 | 0–0.5 | 0–1 | 97–100 |
| 82 | 0–75 | 0–98 | 0–0.5 | 0–6 | 0–5 |
| 90 | 40–70 | 0–0.5 | 0–0.5 | 10–30 | 5–25 |

The process of the present invention may be employed continuously or semi-continuously as necessary to lower the concentration of the acetone in the carbonylation reactor within a predetermined range. As mentioned hereinabove, operation of the carbonylation process with reduced concentrations of acetone permits the production of acetic anhydride of higher quality with respect to the reducing substances specification. We also have found that such lower acetone concentrations result in an increased production rate, an improvement in the color of the acetic anhydride product, a lowered tar formation rate and a decrease in the tendency of the tar formed to bind rhodium. At least a portion of the production rate increase is due simply to the reactor volume made available for more reactants by the lower volume of acetone present. For example, lowering the acetone level to about 1.4 weight percent as described herein results in about 2% increase in production rate due to increased useful reactor volume.

A reduction in the amount of tar produced by the carbonylation process requires the processing of lower amounts of catalyst-tar mixtures, e.g., as described in U.S. Pat. Nos. 4,388,217 and 4,945,075, which reduces significantly the risk of rhodium losses in such processes. Due to the dramatic rise in the cost of rhodium, any process improvements which reduce the risk of its loss in the overall acetic anhydride production system have become increasingly important.

The following examples illustrate the operation of our novel process in conjunction with the acetic anhydride production system described in U.S. Pat. No. 4,374,070 wherein a mixture of methyl iodide and methyl acetate is contacted with carbon monoxide in the presence of a catalyst system comprising rhodium and a lithium salt at a temperature of about 160° to 220° C. and about 21.7 to 83.7 bar absolute (about 300 to 1200 psig). In the carbonylation process, a feed mixture containing methyl acetate is continuously fed to a carbonylation reactor and a reaction product mixture containing acetic anhydride is continuously removed. The feed to the reactor is such as to maintain within the reaction mixture about 500 to 1000 ppm rhodium, about 1500 to 3700 ppm lithium, about 7 to 35 weight percent methyl iodide and about 5 to 40 weight percent acetic acid.

The effluent from the liquid phase carbonylation reactor is processed to remove therefrom unreacted carbon monoxide and other non-condensible gases and catalyst components. Any dimethyl ether fed to the carbonylation reactor which is not converted to methyl acetate is removed as a component of the non-condensible gases. The remainder of the effluent then is fed to a distillation column from which a crude acetic anhydride/acetic acid mixture is obtained. The vaporized low boiler stream removed at or near the top of the distillation column comprises methyl acetate, methyl iodide, acetic acid and acetone The low boiler stream is condensed and all or a portion, typically about 5 to 25 weight percent, of it is subjected to the acetone removal process.

At the commencement of the operation of the acetone removal process, the concentration of the acetone in the reactor was 4.0 to 4.5 weight percent. All parts given are by volume.

EXAMPLE 1

In accordance with the flow diagram of FIG. 1, the above-described low boiler stream is fed at a rate of 16 parts per minute via conduit 10 to the lower, mid. section of distillation column 12 operated at a base temperature of 60° to 65° C. to give an acetic acid underflow stream removed by means of line 16. The vapor removed from the top of column 12 is condensed and the condensate fed at 1.65 parts per minute near the top of extraction column 28. Water is fed near the bottom of extractor 28 at 6.5 parts per minute by means of conduit 32. Methyl iodide having a purity of 98.6% or greater is underflowed from the extraction column through conduit 30.

The aqueous phase is removed near the top of extractor 28 and is fed, via conduit 34, water extract tank 36 and conduit 38, at a rate of 7.5 parts per minute to distillation column 40 maintained by heat source 42 at a base temperature of 98° to 100° C. A vapor stream comprised of methyl acetate, methyl iodide and minor amounts of acetone and water is removed from distillation column 40 and is condensed by condenser 46. A portion of the condensate is returned to the top of the column via conduits 48 and 52 at a rate of 1.5 parts per minute and the remainder is recovered via conduits 48 and 50 at a rate of 0.5 parts per minute. Water containing methyl acetate and acetone is removed from the column by means of line 54 at a rate of about 7.0 parts per minute. Normally, the weight ratio of methyl acetate:acetone removed from the base of the column is in the range of about 4:1 to 2:1.

The compositions of the streams transported by conduits 10, 26, 38, 50 and 54 are given below wherein the methyl acetate (MeOAc), methyl iodide (MeI), acetic acid (HOAc), acetone and water components of each stream are given as weight percentages based on the total weight of the stream. The value given for each component can vary depending on the operation of the distillation column of the acetic anhydride production system from which the low boiling mixture is obtained.

|  | Components | | | | |
|---|---|---|---|---|---|
| Conduit | MeOAc | MeI | HOAc | Acetone | Water |
| 10 | 59.0 | 22.5 | 11.5 | 7.0 | 0 |
| 26 | 14.0 | 82.5 | 0 | 3.0 | 0.5 |
| 38 | 4.5 | 2.5 | 0 | 1.5 | 91.5 |
| 50 | 53.0 | 40.0 | 0 | 4.0 | 3.0 |
| 54 | 3.5 | 0 | 0 | 1.5 | 95.0 |

After operation of the acetone removal process for 30 to 40 days, the acetone concentration of the carbonylation reactor is reduced to 2.0 to 2.5 weight percent. The effect of acetone levels on carbonylation reaction rate, tar formation and quality (reducing substances and color) or refined acetic anhydride obtained from the production system are given in Table I. Acetone Level is the weight percent acetone in the carbonylation reactor, Tar Formation Rate is:

$$\frac{\text{kilograms tar produced}}{\text{million kilograms acetic anhydride produced}}$$

as determined by the amount of tar purged from the acetic anhydride production facility, Reducing Substances are milliequivalents of potassium permanganate consumed in 30 minutes per 100 mL refined acetic anhydride determined spectrophotometrically and Color is the value obtained according to ASTM D-b 1209-84 for the refined acetic anhydride. The Relative Reaction Rate values were determined by (1) dividing the moles of carbon monoxide consumed per hour at each acetone level by the parts per million rhodium present and (2) dividing each value thus obtained by the value obtained at an acetone level of 4 weight percent.

TABLE I

| Acetone Level | Relative Reaction Rate | Tar Formation Rate | Reducing Substances | Color |
|---|---|---|---|---|
| 4.0 | 1.000 | 660 | 0.62 | 11.5 |
| 3.8 | 1.003 | 650 | 0.56 | 10.9 |
| 3.6 | 1.008 | 620 | 0.49 | 10.3 |
| 3.4 | 1.018 | 550 | 0.43 | 8.8 |
| 3.2 | 1.032 | 530 | 0.36 | 8.1 |
| 3.0 | 1.056 | 470 | 0.34 | 7.5 |
| 2.8 | 1.103 | 470 | 0.30 | 6.7 |
| 2.6 | 1.111 | 470 | 0.27 | 6.3 |

EXAMPLE 2

The process of Example 1 is repeated using the extractive distillation embodiment illustrated in FIG. 2. The aqueous phase from extractor 36 is fed by conduit 38 at a rate of 7.5 parts per minute to the sidewall of extractive distillation column 60 at a point approximately 45%, based on the total height of the column, from the bottom of the column. At steady state conditions, the base of column 60 is maintained at a temperature of 91° to 94° C. by means of reboiler 64. A liquid phase is removed from the base of the column by conduit 62 and a portion is fed by mans of conduit 70 at 6.5 parts per minute to column 60 at a point approximately 75% from the bottom of the column. A second portion of the liquid phase is transported via conduits 62, 70, 72, and 32 to the bottom of extractor 28 at the rate of 6.5 parts per minute along with make-up water which is supplied by conduit 74 at the rate of 0.1 parts per minute.

An upper vapor phase is removed from the top of column 60 by means of conduit 76, condensed in condenser 78 and the condensate is recycled at a rate of 0.7 parts per minute by conduits 80 and 82 to the acetic anhydride production system. A lower vapor phase is removed from the bottom of column 60 at a point approximately 20% from the bottom of the column by conduit 86, condensed by condenser 88 and disposed of through conduit 90 at the rate of 0.3 parts per minute.

The compositions of the stream transported by conduits 38, 62, 82 and 90 relative to Example 2 are given below wherein the methyl acetate(MeOAc), methyl iodide (MeI), acetic acid (HOAc), acetone and water components of each stream are given as weight percentages based on the total weight of the streams.

|  | Components | | | | |
|---|---|---|---|---|---|
| Conduit | MeOAc | MeI | HOAc | Acetone | Water |
| 38 | 6.0 | 2.5 | 0 | 1.5 | 90 |
| 62 | 0.5 | 0 | 0 | 0 | 99.5 |
| 82 | 73.0 | 23.5 | 0 | 1.5 | 2.0 |
| 90 | 62.5 | 0 | 0 | 21.5 | 16.0 |

The invention has been described in detail with particular reference to preferred embodiments thereof, but it will be understood that variations and modifications can be effected within the spirit and scope of the invention.

We claim:

1. Process for the removal of acetone from a production system in which acetic anhydride is produced by contacting carbon monoxide with a mixture comprising methyl iodide and methyl acetate and/or dimethyl ether in the presence of a catalyst system and acetic acid by the steps comprising:

(1) obtaining from the production system a low-boiling stream comprising methyl acetate, methyl iodide, acetic acid and acetone;

(2) distilling the stream of Step (1) to obtain:
   (a) an overhead stream comprising methyl acetate, methyl iodide and acetone; and
   (b) an underflow stream comprising methyl acetate, acetone and essentially all of the acetic acid;

(3) extracting the Step(2)(a) stream with water to obtain:
   (a) a methyl iodide phase containing methyl acetate; and
   (b) an aqueous phase containing methyl acetate, methyl iodide and acetone; and (4) distilling the aqueous phase to obtain:
   (a) a vapor phase comprising methyl acetate, methyl iodide and minor amounts of acetone and water; and
   (b) an aqueous stream containing methyl acetate and acetone.

2. Process according to claim 1 wherein Steps (3) and (4) comprise:

(3) feeding the Step (2)(a) stream which contains essentially no acetic acid to the upper portion, and feeding water to the bottom portion, of a column extractor and obtaining (a) a stream of methyl iodide having a purity of at least 90 weight percent from the bottom of the extractor and (b) an aqueous phase containing methyl acetate, methyl iodide and acetone from the top of the extractor; and (4) feeding the Step (3)(b) aqueous stream to the side of a fractional distillation column and obtaining (a) a vapor phase comprising methyl acetate, methyl iodide and minor amounts of acetone and water from the top of distillation column and (b) a liquid stream comprising water, methyl acetate and acetone, wherein the weight ratio of methyl acetate:acetone does not exceed 6, from the bottom of the distillation column.

3. Process of claim 2 wherein (i) the streams of Steps (2)(b) and (3)(a) and vapor phase of Step (4)(a) are recycled to recover at least 95 weight percent of the methyl iodide of the low boiling stream of Step (1) and (ii) the Step (4)(b) liquid stream contains less than 200 parts per million iodine.

4. Process of claim 2 wherein (i) the streams of Steps (2)(b) and (3)(a) and the vapor phase of Step (4)(a) are recycled to recover at least 98 weight percent of the methyl iodide of the low boiling stream of Step (1) and (ii) the Step (4)(b) liquid stream contains less than 100 parts per million iodine.

5. Process according to claim 1 wherein Steps (3) and (4) comprise:

(3) feeding the Step (2)(a) stream which contains essentially no acetic acid to the upper portion, and feeding water to the bottom portion, of a column extractor and obtaining (a) a stream of methyl iodide having a purity of at least 90 weight percent from the bottom of the extractor and (b) an aqueous phase containing methyl acetate, methyl iodide and acetone from the top of the extractor; and (4) feeding the Step (3)(b) aqueous phase to the side of an extractive distillation column, recycling at least a portion of a liquid phase comprising water from the base of the distillation column to the side of the distillation column at a point above the feed of the Step (3)(b) aqueous phase and removing (a) a vapor phase comprising methyl acetate, methyl iodide and minor amounts of acetone and water from the top of distillation column and (b) a vapor stream comprising water, methyl acetate and acetone, wherein the weight ratio of methyl acetate:acetone does not exceed 6, from the lower portion of the distillation column.

6. Process of claim 5 wherein (i) the streams of Steps (2)(b) and (3)(a) and the vapor phase of Step (4)(a) are recycled to recover at least 95 weight percent of the methyl iodide of the low boiling stream of Step (1) and (ii) the Step (4)(b) vapor stream contains less than 200 parts per million iodine.

7. Process of claim 5 wherein (i) the streams of Steps (2)(b) and (3)(a) and the vapor phase of Step (4)(a) are recycled to recover at least 98 weight percent of the methyl iodide of the low boiling stream of Step (1) and (ii) the Step (4)(b) vapor stream contains less than 100 parts per million iodine.

* * * * *